(12) United States Patent
Klapproth

(10) Patent No.: US 7,598,044 B2
(45) Date of Patent: Oct. 6, 2009

(54) PROCEDURE AND DEVICE FOR DETERMINING THE CONCENTRATIONS OF AT LEAST TWO LIGANDS

(75) Inventor: Holger Klapproth, Freiburg (DE)

(73) Assignee: Micronas Holding GmbH, Freiburg i.Br. (DE)

( * ) Notice: Subject to any disclaimer, the term of this patent is extended or adjusted under 35 U.S.C. 154(b) by 291 days.

(21) Appl. No.: 11/397,347

(22) Filed: Apr. 4, 2006

(65) Prior Publication Data

US 2006/0223103 A1   Oct. 5, 2006

(30) Foreign Application Priority Data

Apr. 4, 2005   (EP) .................................. 05007284

(51) Int. Cl.
*G01N 33/53*   (2006.01)
(52) U.S. Cl. ...................... 435/7.1; 435/7.21; 435/283; 436/501; 436/518; 422/50; 422/60
(58) Field of Classification Search ........................ None
See application file for complete search history.

(56) References Cited

U.S. PATENT DOCUMENTS 6,197,503 B1 *   3/2001   Vo-Dinh et al. .................. 435/6

FOREIGN PATENT DOCUMENTS

| WO | WO 92/18866 A1 | | 10/1992 |
| WO | WO 95/18377 A1 | | 7/1995 |
| WO | WO 95/22766 | * | 8/1995 |
| WO | WO 95/22766 A1 | | 8/1995 |
| WO | WO 2004/004455 A2 | | 1/2004 |

* cited by examiner

*Primary Examiner*—Lisa V Cook
(74) *Attorney, Agent, or Firm*—The Webb Law Firm

(57) ABSTRACT

In a procedure for determining the concentrations of ligands contained in a sample wherein a first ligand is bond-specific to a first receptor and a second ligand is bond-specific to a second receptor, the first receptor is immobilized on a first test site and the second receptor is immobilized on a second test site on a substrate. A competitor that is bond-specific to the second receptor is mixed with the sample so that it is present in a predetermined concentration in the mixture. The mixture is brought into contact with the substrate so that the first ligand and the second ligand and/or the competitor bind to the first receptor and the second receptor, respectively. Afterwards the unbound components of the mixture are removed from the substrate. A first metering signal relative to the concentration of the first ligand bound to the first receptor and a second metering signal relative to the concentration of the competitor bound to the second receptor are then generated. The concentrations of the ligands in the sample are determined with reference to the metering signals and the known concentration of the competitor in the mixture.

10 Claims, 4 Drawing Sheets

PROCEDURE AND DEVICE FOR DETERMINING THE CONCENTRATIONS OF AT LEAST TWO LIGANDS

Figure 1:
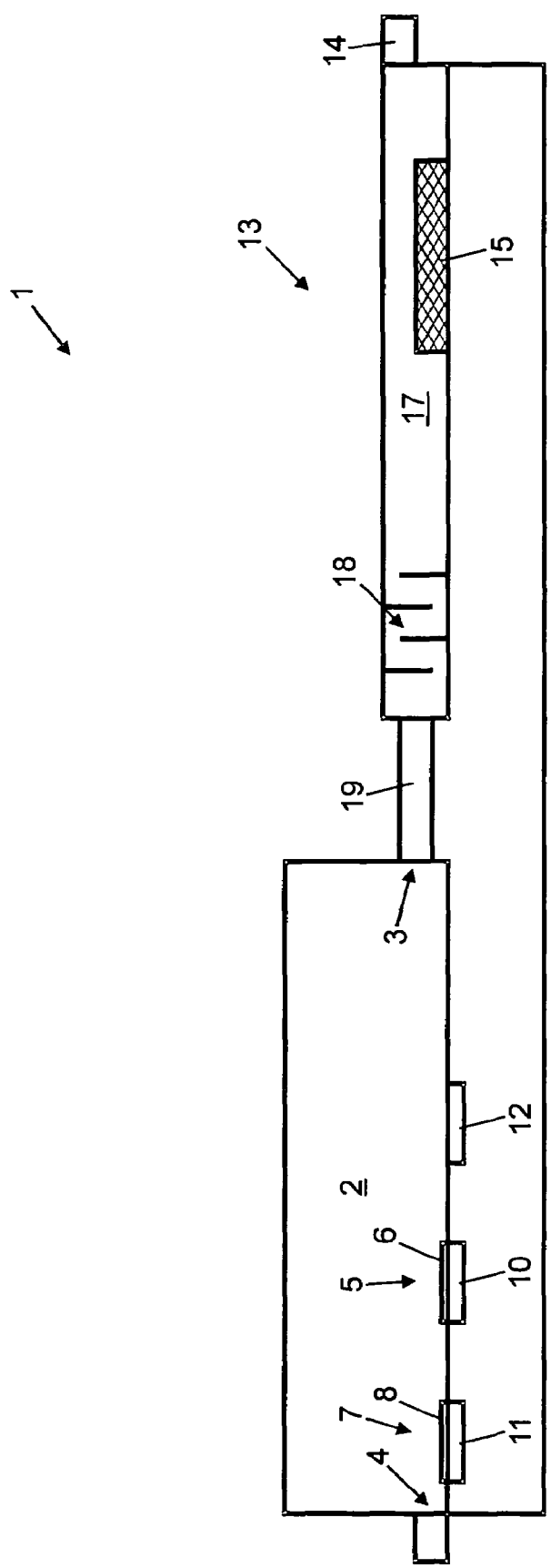

The invention relates to a procedure for determining the concentrations of at least two ligands that are presumed to be contained in a sample for analysis, wherein a first ligand is bond-specific to a first receptor and a second ligand is bond-specific to a second receptor, wherein the first receptor is immobilized on at least a first test site and the second receptor is immobilized on at least a second test site on a substrate. The invention further relates to a device for determining the concentrations of at least two ligands in a sample for analysis, said device comprising a metering chamber with at least one inlet opening and one drain opening, wherein said metering chamber of said device has a substrate on which a first receptor is immobilized on a first test site and a second receptor is immobilized on a second test site, wherein the first receptor is bond-specific to a first ligand and the second receptor is bond-specific to a second ligand, wherein a sensor for capturing a first metering signal relative to the concentration of the ligand bound on the first receptor is arranged on the first test site.

A device of this kind is disclosed in U.S. Pat. No. 6,197,503 B1. Said device comprises a flow-through metering chamber, the underside of which is delimited by an approximately plate-shaped substrate on which a plurality of test sites are arranged, on which test sites receptors are immobilized. The receptors are each bond-specific for a specific ligand contained in a sample for analysis. A semiconductor chip is provided on the back side of the substrate, which chip has an optic sensor on each of the individual test sites. The device comprises an optic radiation source for stimulating the emission of a beam of light relative to the bonding of the ligands on the receptors, the receptors being arranged in the irradiation zone of said radiation source. To determine the concentration of the ligands, the sample is introduced through an inlet opening into the metering chamber so that the ligands contained in the sample can bind to the receptors. After a predetermined exposure time, components of the sample not bound to a receptor are removed from the metering chamber. The exposure time is selected so that, after the removal of the unbound components, only part of the binding sites of a receptor on each of the individual test sites are bound to the ligands that are bond-specific to the given receptor. The proportion of the bound binding sites to the free binding sites is thus relative to the concentration of the given ligands in the sample.

In another step of the procedure, a solution containing detection antibodies marked with a marker is introduced into the metering chamber. The detection antibodies are bond-specific to the ligands and bind thereon. Afterwards the solution is removed from the metering chamber in order to irradiate the test sites with excitation radiation via the radiation source. The detection antibodies indirectly bound via the ligands to the receptors are stimulated by the excitation radiation to emit a beam of light with a different wavelength from that of the excitation radiation. Via the optic sensors, which are sensitive to the beam of light and not sensitive to the excitation radiation, a metering signal is generated for each test site relative to the beam of light and thus the concentration of the ligands in the sample.

A disadvantage of the device is that it only enables a simultaneous determination of the individual concentration values of the various ligands contained in the sample for a limited range of concentrations. In certain samples, for example blood samples, the concentrations of the ligands contained therein may vary by as much as six orders of magnitude. In order to be able to determine a concentration value for the ligand with the lowest concentration as well as for the ligand with the highest concentration in such a sample, without all existing receptor binding sites on one of the test sites binding to a ligand and thus driving the corresponding measurement value to the limit, at least two assays are conducted. A short exposure time is selected for a first assay to determine the concentration of the ligand having the highest concentration value, and a considerably longer exposure time than for the first assay is selected in a second assay to determine the concentration of the ligand having the lowest concentration value. The disadvantage therein is that a new semiconductor chip is needed for each assay, which in turn makes the measurement expensive and labor-intensive to perform. Another disadvantage is that a relatively large sample is required. For the examination of blood samples, which are drawn from a patient's finger by means of a puncturing device, this can mean that blood must be drawn from at least two places from the finger, which can be especially difficult with children.

The object of the invention is therefore to design a device and a procedure of the aforementioned kind by which the concentrations of a plurality of the ligands presumed to be contained in a sample for analysis can be measured easily, rapidly and inexpensively.

This objective is solved for the invention as follows: A competitor that is bond-specific to the second receptor is mixed with the sample so that the competitor is contained in a predetermined concentration in the mixture thus obtained; the mixture is brought into contact with the substrate so that the first ligand can bind to the first receptor and the second ligand and/or the competitor can bind on the second receptor, and afterwards the components of the mixture not bound to an immobilized receptor are removed from the substrate, and then a first metering signal is generated relative to the concentration of the first ligand bound to the first receptor and a second metering signal is generated relative to the concentration of the competitor bound to the second receptor, and wherein the concentration of the first ligand in the sample can be determined with reference to the first metering signal and the concentration of the second ligand in the sample can be determined with reference to the second metering signal and the known concentration of the competitor in the mixture. The ligands and/or receptors can comprise nucleic acids or their derivatives (DNA, RNA, PNA, LNA, oligonucleotides, plasmids, chromosomes), peptides, proteins (enzymes, proteins, oligopeptides, cellular receptor proteins and complexes thereof, peptide hormones, antibodies and fragments thereof), carbohydrates and their derivatives, in particular glycolized proteins and glycosides, fats, fatty acids and/or lipids.

In an advantageous manner it is thus possible, through the combination of the competitive assay with a non-competitive assay, to determine the concentrations the individual ligands in samples containing a plurality of ligands of widely varying concentrations in the same metering chamber with only a single test. The concentration of the competitor in the mixture of the sample and the competitor and the exposure time during which the mixture remains in contact with the receptors are calibrated to the concentration ranges to be tested for the individual ligands so that, after the components of the mixture not bound to a receptor are removed, only part of the binding sites on all test sites bind receptors to a ligand, if said ligand is contained in the sample in the concentration range to be checked. The concentration of the competitor in the sample is preferably selected so that it corresponds to a threshold value of the concentration of the second ligand, from which a statement such as "good/bad" or "ill/healthy" can be inferred. With the procedure according to the invention, a plurality of ligand concentrations ranging from g/l to µg/l can be detected at the same time in a flow cell or similar metering chamber.

In an advantageous embodiment of the invention, a detection antibody that is bond-specific to the first ligand and marked with a first marker is brought into contact with the first test site, wherein afterwards markers not bound to an immobilized receptor are removed from the substrate, and wherein afterwards the first metering signal is generated relative to the concentration of the first marker. The concentration of the first ligand can thus be measured by means of a sandwich ELISA.

In a preferred embodiment of the invention, the competitor is marked with a second marker, wherein the second metering signal is generated relative to the concentration of the second marker bound to the second receptor after the components of the mixture not bound to an immobilized receptor are removed from the substrate. In doing so, the second marker can coincide with the first marker.

It is advantageous if the first marker and/or the second marker are enzymes/is an enzyme, if said enzyme is brought into contact with at least two chemicals during the capture of the metering signal, between which chemicals a chemical redox reaction takes place in the presence of the enzyme, and if the first metering signal and/or the second metering signal are/is generated by measuring a redox potential. The redox potential can be measured by means of an ISFET.

In a functional embodiment of the invention, the first marker and/or the second marker are/is irradiated with excitation radiation during the capture of the metering signals, which radiation excites the marker(s) to emit a beam of light, wherein the first metering signal and/or the second metering signal are/is generated by measuring the beam of light emitted from the respective marker. In doing so, the excitation radiation can be generated by a light source, exemplarily a light emitting diode and/or a xenon lamp. The same excitation radiation is preferably used for the first marker and the second marker. It is also conceivable, however, that the first and second markers are different dyes, such as Cy3 and Cy5, and that these dyes are excited with different wavelengths.

It is advantageous if the first test site and/or the second test site are/is brought into contact with a chemiluminescent substrate during the capture of the metering signal, which substrate is excited to emit light relative to the bond of the first ligand to the first receptor and/or relative to the bond of the competitor to the second receptor, wherein the first metering signal and/or the second metering signal are/is generated by measuring the beam of light emitted from the respective test site. In doing so, the beam of light is generated by chemical means without excitation radiation.

The aforementioned task is solved for the device as follows: Said device comprises a mixing device connected with an infeed opening for the sample and a receiving space containing the competitor for mixing the sample with a competitor that is bond-specific to the second receptor, said mixing device has an outfeed opening for the mixture comprising the sample and the competitor, which outfeed opening is connected with the inlet opening of the metering chamber; the mixing device is configured so that the competitor is present in a predetermined concentration in the mixture, the second sensor is configured to capture a second metering signal relative to the concentration of the competitor bound to the second receptor and it is connected to a computer configured to determine the concentration of the second ligand in the sample from the second metering signal and the concentration of the competitor in the mixture.

Prior to entering the metering chamber, the sample is thus mixed by means of the mixing device with a competitor that is bond-specific to the second receptor, so that a competitive assay can be conducted for the second ligand simultaneously with a non-competitive assay for the first ligand in the mixing chamber. As has already been explained for the procedure, the combination of these assays in one sample comprising a plurality of ligands varying widely in their concentrations makes it possible to determine the concentrations of the individual ligands with a single test.

It is advantageous if the competitor is stabilized in gel, paste or solid form in the receiving space, preferably so that it clings to a wall of the receiving space, and if the receiving space for dissolving the competitor in the sample is configured as a flow-through mixing chamber, through which the infeed opening for the sample is connected to the inlet opening of the metering chamber. This makes the device very easy to handle. The stabilization of the competitor preferably comprises at least one non-reducing disaccharide and at least one LEA class protein or polypeptide. The non-reducing disaccharide can be selected from a group that is in turn selected from trehaose (D-glucopyranosyl-D-glucopyranose), sucrose (β-D-fructofuranosyl-α-D-glucopyranosid) as well as derivatives thereof. A stabilization of this kind is described in WO 2004/004455 A2. The competitor has a long storage life in stabilized form.

In a preferred embodiment of the invention, the flow-through mixing chamber comprises a mixing structure configured so that the mixture is preferably diverted in alternating, opposite directions as it flows through the flow-through mixing chamber, and that said mixing structure is arranged between the competitor in gel, paste or solid form and the inlet opening of the metering chamber. The mixer can thus be a so-called Mobius mixer, which can be manufactured with very compact dimensions using the methods of microsystem technology.

In a functional embodiment of the invention, the sensor are optic sensors, wherein the first receptor for detecting a first beam of light emitted relative to the bond of the first ligand on said first receptor is preferably arranged directly on the first sensor and/or the second receptor for detecting a second beam of light emitted relative to the bond of the competitor on said second receptor is/are preferably arranged directly on the second sensor. The beam of light generated on the receptors can thus be transmitted directly to the sensor(s) without the detour via a convex lens.

It is advantageous if the competitor is marked with a marker that emits a beam of light when it is irradiated with excitation radiation, if the device for irradiating the second test site with excitation radiation has at least one radiation source, and if the second sensor is sensitive to the beam of light and not sensitive to the excitation radiation. In doing so, the radiation source can also be arranged outside of the metering chamber, if said metering chamber has at least one wall area transparent to the excitation radiation.

The device can be a component of a kit according to one of claims 6 through 10, which can comprise, in addition to said device a detection antibody that is bond-specific to the first ligand and marked with an enzyme or similar marker, at least two chemicals, between which a chemical redox reaction occurs upon contact with the detection antibody and/or the competitor and/or the enzyme arranged on the detection antibody, and/or a chemiluminescent substrate in which a light-emitting chemical reaction is triggered upon contact with the enzyme arranged on the detection antibody and or the competitor, and/or a radiation source for emitting the beam of light, arranged on the first test site.

The marker, the chemiluminescent substrate and/or the chemicals can be fed into the metering chamber with a suitable infeeding device such as, e.g. a micropump or a pipette.

Figure 2:
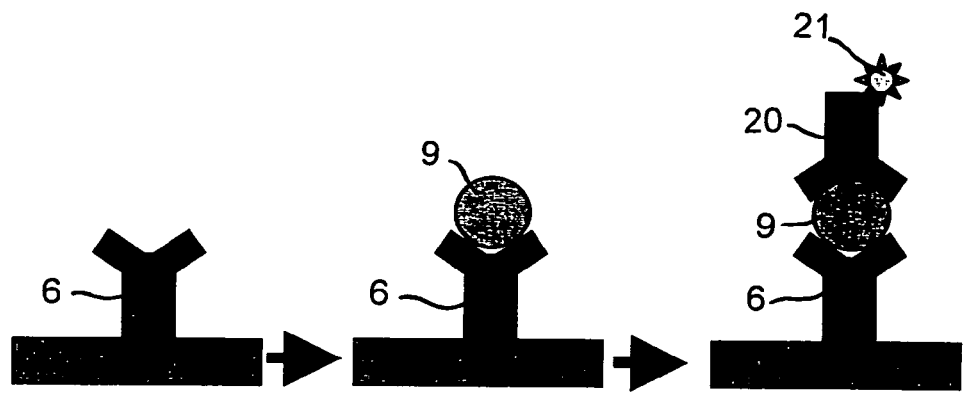
Figure 3:
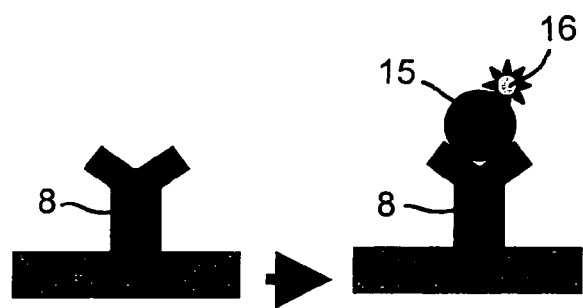
Figure 4:
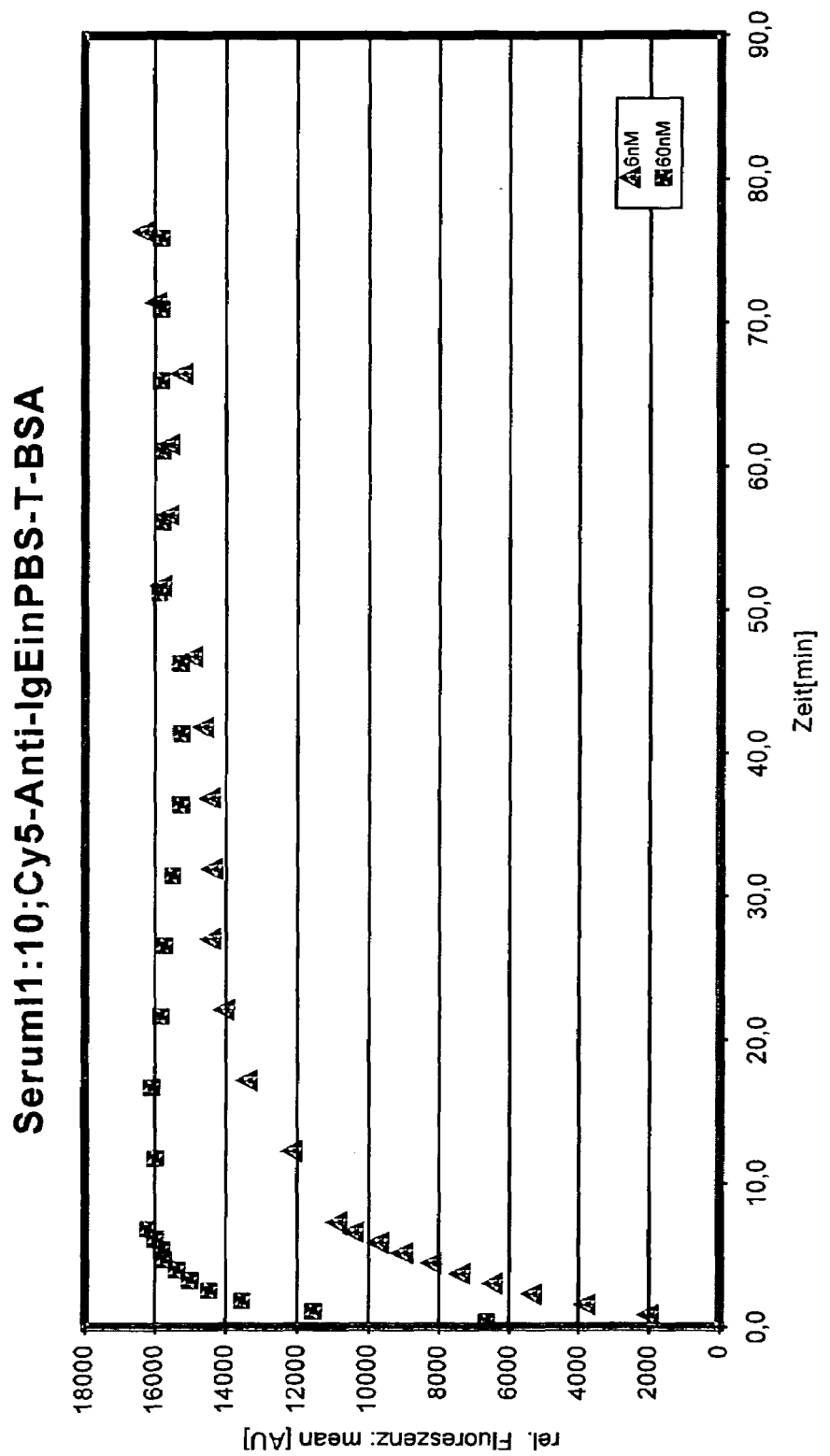
Figure 5:
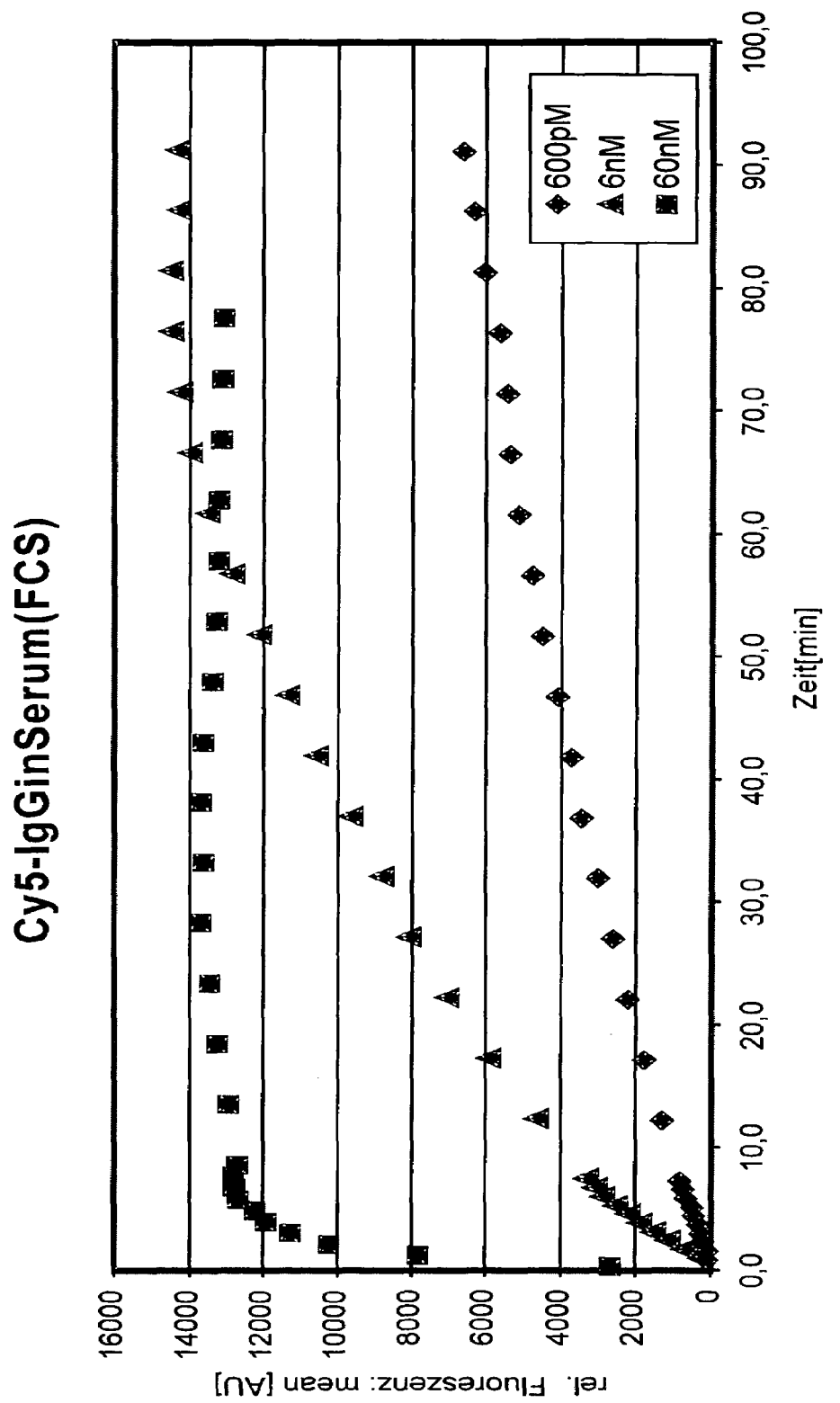

In the following, an exemplary embodiment of the invention is explained in more detail with reference to the drawing, in which:

FIG. 1 shows a longitudinal section of a device for determining the concentration of ligands contained in a sample for analysis, FIG. 2 shows a schematic illustration of a sandwich ELISA, FIG. 3 shows a schematic illustration of a competitive ELISA, FIG. 4 shows a graph of the measurements of the concentration of a ligand marked with Cy5 determined with two sandwich ELISAs, wherein the time is plotted on the abscissa and the measurement amplitude is plotted on the ordinate and wherein the concentration is given as a parameter, and FIG. 5 shows a graph of the measurements of the concentration of a ligand marked with Cy5 determined with three direct ELISAs, wherein the time is plotted on the abscissa and the measurement amplitude is plotted on the ordinate and wherein the concentration is given as a parameter.

A device, designated in its entirety by the number 1 in FIG. 1, for determining the concentrations of at least two ligands in a sample for analysis comprises a metering chamber 2 configured as a flow cell, which has an inlet opening 3 and a drain opening 4. A wall of said metering chamber 2 is formed from a semiconductor substrate, on which a first receptor 6 is immobilized on a first test site 5 and a second receptor 8 is immobilized on a second test site 7 laterally spaced from said first-test site. The first receptor 6 is bond-specific to a first ligand 9 contained in the sample for analysis and the second receptor 8 is bond-specific for a second ligand contained in the sample for analysis. The second ligand has a greater concentration in the sample than the first ligand 9.

A first optic sensor 10 is integrated in the semiconductor substrate directly underneath the first receptor 6 on the first test site 5 and a second optic sensor 11 is integrated in the semiconductor substrate directly underneath the second receptor 8 on the second test site 7. In addition, a third optic sensor 12 is arranged in the wall of the metering chamber, which sensor is not covered with a receptor and serves as a reference value encoder. The sensors 10, 11, 12 are exemplarily photodiodes.

The device 1 further comprises a mixing device 13, which connects the inlet opening 3 of the metering chamber 2 with an infeed opening 14. The function of the mixing device 13 is to mix the sample with a competitor 15 that is bond-specific to the second receptor 8, said competitor being marked with an enzyme 16, exemplarily HRP (horse radish peroxidase). In order to do this, the sample is introduced through the infeed opening 14 into a receiving space 16 [sic] of the mixing device 13 by means of, e.g., a pipette or pump. In the receiving space 17, the marked competitor 15 in stabilized form is arranged relative to the infeed opening 14 so that the sample, as it is being/after it has been introduced in the receiving space 17, comes into contact with the competitor 15 or the enzyme 16 bound thereto and mixes with the competitor-enzyme-complexes. Upstream from the receiving space 17 relative to the flow direction, the mixing device 13 comprises a mixing structure 18 configured as a Mobius mixer, said mixing structure being connected by its one end to the receiving space 17 and by its other end via a channel 19 to the inlet opening 3 of the metering chamber 2, said other end comprising a drain opening for the mixture formed from the sample and the competitor-enzyme-complexes.

The mixing device 13 is configured so that the competitor 15 in the mixing chamber 2 [sic] is present in the mixture in a predetermined concentration corresponding to a threshold to be measured. This is accomplished by the metering chamber 2 and the mixing device 13 having a predefined volume, and by selecting the quantity of the competitor 15 stabilized in the receiving space 17 so that the desired concentration is automatically achieved when said competitor 15 and the sample are blended into a mixture of the predefined volume.

After the metering chamber 2 is filled with the mixture of the sample and the competitor-enzyme-complexes, a specified time period is allowed for the ligands contained in the mixture and the competitor 15 to bind on their respective bond-specific receptors 6, 8. The first time period is selected so that only part of the free binding sites of the receptors 6, 8 on each of the respective test sites 5, 7 binds to a ligand. The binding of a molecule of the first ligand 9 on the first receptor 6 and the binding of a competitor-enzyme-complex on the second receptor 8 are schematically illustrated in FIG. 2 and FIG. 3, respectively.

After the first specified time period has elapsed, a rinsing fluid is flushed through the metering chamber 2 via the infeed opening 14, the inlet opening 3 and the drain opening 4 in order to remove those mixture components not bound to a receptor 6, 8 from the metering chamber 2.

Afterwards a solution containing a detection antibody 20 that is bond-specific to the first ligand 9 and marked with an enzyme 21, exemplarily HRP, is introduced in the metering chamber 2. After the detection antibody 20 is introduced into the metering chamber 2, a specified second time period, so selected that nearly all of the molecules of the first ligand 9 bound to the first receptor 6 each bind to a molecule of the detection antibody 20 and thus become indirectly marked with the enzyme 21, is allowed to elapse.

After the specified time period has elapsed, the rinsing fluid is once more flushed through the metering chamber 2 in order to remove the detection antibody 20 not bound to a first ligand from said metering chamber 2.

Afterwards, a chemiluminescent substrate containing hydrogen peroxide and a chemiluminophor, such as luminol, is introduced into the metering chamber 2 via the infeed opening 14 and the inlet opening 3. When the enzymes 16, 21 come into contact with the hydrogen peroxide, free oxygen radicles are split from the hydrogen peroxide, which cause the chemiluminophor to emit light as it is being chemically broken down. The light is thus generated relative to the bond of the first ligand on the first receptor 6 on one hand and relative to the bond of the competitor 15 on the second receptor 8 in the metering chamber 2 on the other hand.

The optic sensors 10, 11 are sensitive to the light and so arranged in relation to the receptors 6, 8 so that they only detect the light emitted on their respective, allocated test site 5, 7, but not the light emitted from the other respective test site 7, 5.

A computer (not shown in the drawing) is connected to the sensors 10, 11, which computer determines the concentration of the first ligand 6 in the sample relative to the metering signal of the first sensor 10 and the concentration of the second ligand in the sample relative to the metering signal from the second sensor 11 and the known concentration of the competitor 15 in the mixture, with reference to the law of mass action. The computer can be integrated as an electric circuit in the substrate or the wall of the metering chamber 2.

The measurements obtained with a direct ELISA and a sandwich ELISA are graphed as a function of time in FIG. 4 and FIG. 5. In the ELISA, a beam of light is emitted relative to the bond of the first ligand on the one receptor and relative to the bond of the second ligand on another receptor. For this purpose, the ligands are marked with a marker, such as the dye Cy5, and irradiated with excitation radiation that excites the marker to emit light. It can be clearly seen that the rise in measurement values levels off as the concentration of the ligands in the sample decreases. With the procedure according to the invention, it is possible to measure the concentrations of two ligands contained in a sample in very different concentrations simultaneously in the metering chamber 2. This is accomplished by measuring the concentration of the ligand having the high concentration by means of a competitive assay and the concentration of the ligand 9 having the low concentration by means of a non-competitive assay, so that neither sensor 10, 11 reaches the limit when recovering the metering signal.

The invention claimed is:

1. A device for determining the concentrations of at least two ligands in a sample for analysis, with a metering chamber comprising at least one inlet opening and a drain opening, said metering chamber having a substrate on which a first receptor and a second receptor are immobilized on a first test site and a second test site, respectively, wherein said first receptor and said second receptor are bond-specific for a first ligand and a second ligand, respectively, and wherein a competitor is bond-specific for said second receptor, wherein a first sensor to capture a first metering signal relative to the concentration of the ligand bound to the first receptor and a second sensor are arranged on the first test site and the second test site, respectively, wherein the device comprises a mixing device for mixing the sample with the competitor that is bond-specific to the second receptor, which mixing device is connected to an infeed opening for the sample and a receiving space containing the competitor; that the mixing device comprises an outlet opening for the mixture comprising the sample and the competitor, said outlet opening being connected to the inlet opening of the metering chamber; that the mixing device is configured so that the competitor is present in the mixture in a predetermined concentration; that the second sensor is configured to capture a second metering signal relative to the concentration of the competitor bound to the second receptor and is connected to a computer, which computer is configured to determine the concentration of the second ligand in the sample from the second metering signal and from the concentration of the competitor in the mixture.

2. A device according to claim 1, wherein the competitor is stabilized in gel, paste or solid form in the receiving space, preferably so that it adheres to a wall of said receiving space, and that said receiving space is configured as a flowthrough mixing chamber to dissolve the competitor in the sample, via which chamber the infeed opening for the sample is connected to the inlet opening of the metering chamber.

3. A device according to claim 1, wherein the flow-through mixing chamber comprises a mixing structure configured so that the mixture is diverted in alternately opposite directions as it flows through the flow-through mixing chamber, and that said mixing structure is arranged between the competitor that is in a gel, paste or solid form and the inlet opening of the metering chamber.

4. A device according to claim 1, wherein the sensors are optic sensors, and that the first receptor for detecting a first beam of light emitted relative to the bond of the first ligand on said first receptor is preferably arranged directly on the first sensor and/or the second receptor for detecting a second beam of light emitted relative to the bond of the competitor on said second receptor is preferably arranged directly on the second sensor.

5. A device according to claim 2, wherein the competitor is marked with a marker, which can be excited to emit a beam of light by irradiation with excitation radiation, that said device comprises at least one radiation source for irradiating the second test site with excitation radiation, and that the second sensor is sensitive to the beam of light and not sensitive to the excitation radiation.

6. A kit for performing a procedure for determining the concentrations of at least two ligands presumed to be contained in a sample for analysis, comprising
a device according to claim 1, in which the first sensor is configured as a sensor for measuring a redox potential,
a detection antibody that is bond specific to the first ligand and marked with an enzyme and
at least two chemicals between which a chemical redox reaction takes place upon contact with the enzyme.

7. A kit for performing a procedure for determining the concentrations of at least two ligands presumed to be contained in a sample for analysis, comprising
a device according to claim 1,
a detection antibody that is bond-specific to the first ligand and marked with an enzyme and
a chemiluminescent substrate, in which a chemical reaction is triggered upon contact with the enzyme, in which reaction a beam of light is emitted to which the first sensor is sensitive.

8. A kit for performing a procedure for determining the concentrations of at least two ligands presumed to be contained in a sample for analysis, comprising
a detection antibody that is bond-specific to the first ligand and marked with a marker that can be excited to emit a beam of light when irradiated with excitation radiation,
a device according to claim 1, in which the first sensor is sensitive to the beam of light and not sensitive to the excitation radiation, and
a radiation source arranged on the first test site for emitting the beam of light.

9. A kit for performing a procedure for determining the concentrations of at least two ligands presumed to be contained in a sample for analysis, comprising
a device according to claim 1, in which the competitor is marked with an enzyme and in which the second sensor is configured for measuring an electric redox potential, and
at least two chemicals, between which a chemical redox reaction takes place upon contact with the enzyme.

10. A kit for performing a procedure for determining the concentrations of at least two ligands presumed to be contained in a sample for analysis, comprising
a device according claim 1, in which the competitor is marked with an enzyme, and
a chemiluminescent substrate, in which a chemical reaction is triggered upon contact with the enzyme, in which reaction a beam of light is emitted to which the second sensor is sensitive.

* * * * *

UNITED STATES PATENT AND TRADEMARK OFFICE
CERTIFICATE OF CORRECTION

PATENT NO. : 7,598,044 B2  Page 1 of 1
APPLICATION NO. : 11/397347
DATED : October 6, 2009
INVENTOR(S) : Holger Klapproth It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this

Twenty-eighth Day of September, 2010

David J. Kappos
*Director of the United States Patent and Trademark Office*